United States Patent [19]
Ben-haim

[11] Patent Number: 5,568,809
[45] Date of Patent: Oct. 29, 1996

[54] APPARATUS AND METHOD FOR INTRABODY MAPPING

[75] Inventor: Shlomo Ben-haim, Haifa, Israel

[73] Assignee: Biosense, Inc., Orangeburg, N.Y.

[21] Appl. No.: 490,122

[22] Filed: Jul. 12, 1995

Related U.S. Application Data

[60] Continuation of Ser. No. 311,598, Sep. 23, 1994, abandoned, which is a division of Ser. No. 94,539, Jul. 20, 1993, Pat. No. 5,391,199.

[51] Int. Cl.⁶ .................................................. A61M 25/095
[52] U.S. Cl. ............................................................. 128/656
[58] Field of Search ................................... 128/639, 642, 128/653.4, 654, 656, 657, 658, 662.05, 662.06

[56] References Cited

U.S. PATENT DOCUMENTS

| | | |
|---|---|---|
| 4,304,239 | 12/1981 | Perlin . |
| 4,431,005 | 2/1984 | McCormick ........................... 128/656 |
| 4,444,195 | 4/1984 | Gold . |
| 4,522,212 | 6/1985 | Gelinas et al. . |
| 4,573,473 | 3/1986 | Hess . |
| 4,628,937 | 12/1986 | Hess et al. . |
| 4,649,924 | 3/1987 | Taccardi . |
| 4,699,147 | 10/1987 | Chilson et al. . |
| 4,777,955 | 10/1988 | Brayton et al. . |
| 4,899,750 | 2/1990 | Ekwall . |
| 4,922,912 | 5/1990 | Watanabe . |
| 4,940,064 | 7/1990 | Desai . |
| 5,000,190 | 3/1991 | Petre . |
| 5,025,786 | 6/1991 | Siegel . |
| 5,054,492 | 10/1991 | Scribner et al. .................... 128/662.06 |
| 5,104,393 | 4/1992 | Isner et al. . |
| 5,154,501 | 10/1992 | Svenson et al. . |
| 5,156,151 | 10/1992 | Imran . |
| 5,158,092 | 10/1992 | Glace . |
| 5,161,536 | 11/1992 | Vilkomerson et al. ............. 128/662.05 |
| 5,172,699 | 12/1992 | Svenson et al. . |
| 5,220,924 | 6/1993 | Frazin . |
| 5,222,501 | 6/1993 | Ideker et al. . |
| 5,246,016 | 9/1993 | Lieber et al. . |
| 5,297,549 | 3/1994 | Beatty et al. . |

FOREIGN PATENT DOCUMENTS 0499491 8/1992 European Pat. Off. .

OTHER PUBLICATIONS

Josephson et al., Ventricular Tachycardia during Endocardial Pacing. II. Role of Pace–Mapping to Localize Origin of Ventricular Tachycardia, The American Journal of Cardiology, vol. 50, pp. 11–22, Jul. 1982.

Witkowski et al., An Automated Simultaneous Transmural Cardiac Mapping System, American Journal of Physiology, vol. 247, pp. H661–H668, 1984.

Fann et al., Endocardial Activation Mapping and Endocardial Pace–Mapping Using a Balloon Apparatus, American Journal of Cardiology, vol. 55, pp. 1076–1083, Apr. 1, 1985.

(List continued on next page.)

*Primary Examiner*—George Manuel
*Attorney, Agent, or Firm*—Cowan, Liebowitz & Latman, P.C.

[57] ABSTRACT

This invention concerns an apparatus and method for the treatment of cardiac arrhythmias. More particularly, this invention is directed to a method for ablating a portion of an organ or bodily structure of a patient, which comprises obtaining a perspective image of the organ or structure to be mapped; advancing one or more catheters having distal tips to sites adjacent to or within the organ or structure, at least one of the catheters having ablation ability; sensing the location of each catheter's distal tip using a non-ionizing field; at the distal tip of one or more catheters, sensing local information of the organ or structure; processing the sensed information to create one or more data points; superimposing the one or more data points on the perspective image of the organ or structure; and ablating a portion of the organ or structure.

58 Claims, 9 Drawing Sheets

OTHER PUBLICATIONS

Hauer et al., Endocardial Catheter Mapping: Wire Skeleton Techniques for Representation of Computed Arrhythmogenic Sites Compared with Intraoperative Mapping, Circulation, vol. 74, No. 6, pp. 1346–1354, Dec. 1986.

Pogwizd et al., Reentrant and Nonreentrant Mechanisms Contribute to Arrhythmogenesis During Early Myocardial Ischemia: Results Using Three–Dimensional Mapping, Circulation Research, vol. 61, No. 3, pp. 352–371, Sep. 1987.

Huang et al., Radiofrequency Catheter Ablation of the Left and Right Ventricles: Anatomic and Electrophysiologic Observations, Pace, vol. 11, pp. 449–459, Apr. 1988.

Jackman et al., New Catheter Techniques for Recording Left Free–Wall Accessory Atrioventricular Pathway Activation, Circulation, vol. 78, No. 3, pp. 598–611, Sep. 1988.

Page, Surgical Treatment of Ventricular Tachycardia: Regional Cryoablation Guided by Computerized Epicardial and Endocardial Mapping, Circulation, vol. 80, (Supplement I), No. 3, pp. I–124–I–134, Sep. 1989.

Tweddell et al., Potential Mapping in Septal Tachycardia: Evaluation of a New Intraoperative Mapping Technique, Circulation, vol. 80 (Supplement I), No. 3, pp. I–97–I–108, Sep. 1989.

Shenasa et al., Cardia Mapping, Part I: Wolff–Parkinson–White Syndrome, Pace, vol. 13, pp. 223–230, Feb. 1990.

Scheinman et al., Current Role of Catheter Ablative Procedures in Patients with Cardiac Arrhythmias, Circulation, vol. 83, No. 6, pp. 2146–2153, Jun. 1991.

Buckles et al., Computer–Enhanced Mapping of Activation Sequences in the Surgical Treatment of Supraventricular Arrhythmias, Pace, vol. 13, Pt. 1, pp. 1401–1407, Nov. 1990.

Tanigawa et al., Prolonged and Fractionated Right Atrial Electrograms During Sinus Rhythm in Patients with Paroxysmal Atrial Fibrillation and Sick Sinus Node Syndrome, Journal of American College of Cardiologists, vol. 17, No. 2, pp. 403–408, Feb. 1991.

Kaltenbrunner et al., Epicardial and Endocardial Mapping of Ventricular Tachycardia in Patients with Myocardial Infarcation, Circulation, vol. 83, No. 3, pp. 1058–1071, Sep. 1991.

Masse et al., A Three–Dimensional Display for Cardiac Activation Mapping, Pace, vol. 14, Pt. 1, pp. 538–545, Apr. 1991.

Desai et al., Orthogonal Electrode Catheter Array for Mapping of Endocardial Focal Site of Ventricular Activation, Pace, vol. 14, Pt. 1, pp. 557–574, Apr. 1991.

Pollak et al., Intraoperative Identification of a Radiofrequency Lesion Allowing Validation of Catheter Mapping of Ventricular Tachycardia with a Computerized Balloon Mapping System, Pace, vol. 15, pp. 854–858, Jun. 1992.

Chen et al., Reappraisal of Electrical Cure of Atrioventricular Nodal Reentrant Tachycardia—Lesions from a Modified Catheter Ablation Technique, International Journal of Cardiology, vol. 37, pp. 51–60, 1992.

Chen et al., Radiofrequency Catheter Ablation for Treatment of Wolff–Parkinson–White Syndrome—Short–and Long–Term Follow–up, International Journal of Cardiology, vol. 37, pp. 199–207, 1992.

Scheinman, North American Society of Pacing and Electrophysiology (NASPE) Survey on Radiofrequency Catheter Ablation: Implications for Clinicians, Third Party Insurers, and Government Regulatory Agencies, Pace, vol. 15, pp. 2228–2231, Dec. 1992.

Silka et al., Phase Image Analysis of Anomalous Ventricular Activation in Pediatric Patients with Preexcitation Syndromes or Ventricular Tachycardia, American Heart Journal, vol. 125, No. 2, Pt. 1, pp. 372–380, Feb. 1993.

Josephson, Clinical Cardiac Electrophysiology: Techniques and Interpretations, 2nd Ed., pp. 566–580, 608–615, 770–783, Lea & Febiger, Malvern, Pa., 1993.

Kuchar et al., Electrocardiographic Localization of the Site of Ventricular Tachycardia in Patients with Prior Myocardial Infarction, JACC, vol. 13, No. 4, pp. 893–900.

Holt et al., Ventricular Arrhythmias—A Guide to Their Localization, British Heart Journal, vol. 53, pp. 417–430, 1985.

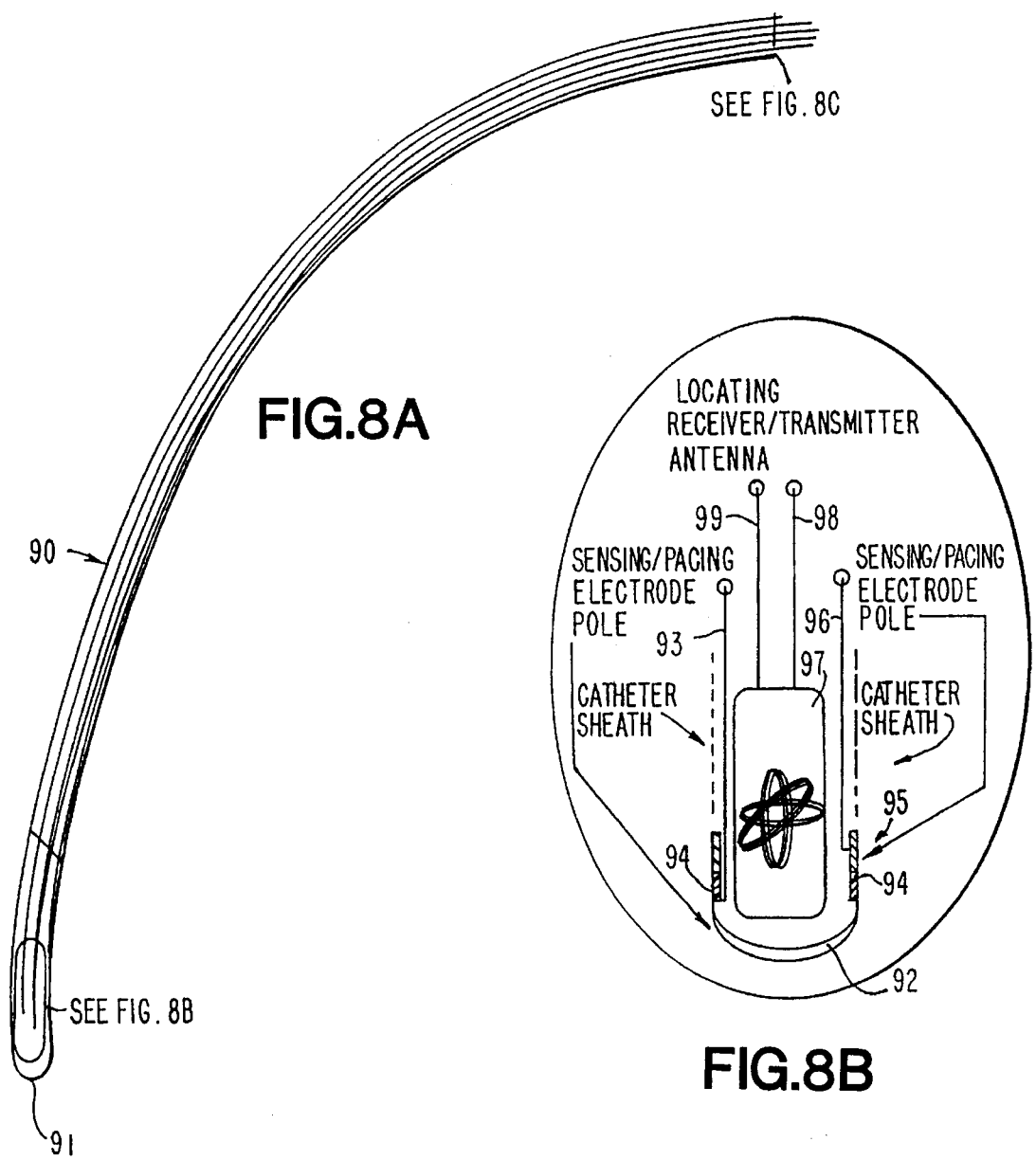
FIG.8A
FIG.8B
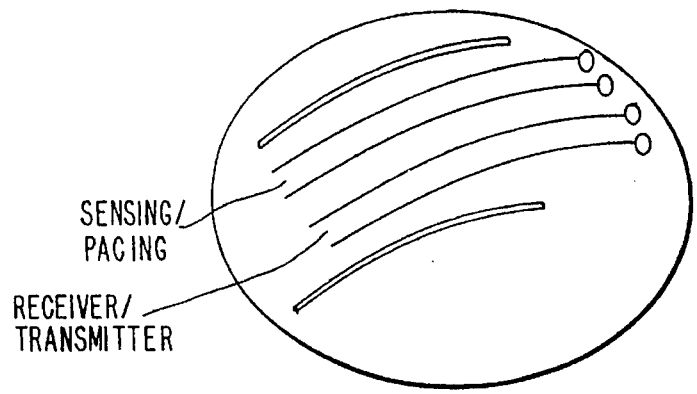
FIG.8C

APPARATUS AND METHOD FOR INTRABODY MAPPING

RELATED PATENT APPLICATION

This application is a continuation of application Ser. No. 08/311,598, filed Sep. 23, 1994 now abandoned which is a divisional of U.S. patent application Ser. No. 08/094,539, filed Jul. 20, 1993 now U.S. Pat. No. 5,391,199.

FIELD OF THE INVENTION

This invention is directed to an apparatus and method for treating a cardiac arrhythmia such as ventricular tachycardia. More particularly, this invention is directed to an improved apparatus and method whereby there is faster identification of an active site to be ablated.

BACKGROUND OF THE INVENTION

Cardiac arrhythmias are the leading cause of death in the United States. The most common cardiac arrhythmia is ventricular tachycardia (VT), i.e., very rapid and ineffectual contractions of the heart muscle. VT is the cause death of approximately 300,000 people annually.

In the United States, from 34,000 to 94,000 new patients are diagnosed annually with VT. Patients are diagnosed with VT after either (1) surviving a successful resuscitation after an aborted sudden death (currently 25–33% of sudden death cases) or (2) syncope, i.e., temporary loss of consciousness caused by insufficient cerebral circulation. The number of VT patients is expected to increase in the future, estimated to range between 61,000 and 121,000 patients annually in five years, as a result of early detection of patients at risk for sudden death by newly developed cardiac tests, advances in cardiopulmonary resuscitation, better medical management of acute myocardial infarction patients, and the demographic shift to a more aged population.

Without proper treatment most patients diagnosed with VT do not survive more than two years. The most frequent current medical treatment consists of certain antiarrhythmic drugs or implantation of an automatic implantable cardiac defibrillator (AICD). Drug treatment is associated with an average life span of 3.2 years, a 30% chance of debilitating side effects, and an average cost of approximately $88,000 per patient. In contrast, AICD implantation is associated with a life expectancy of 5.1 years, a 4% chance of fatal complications, and a cost of approximately $121,000 per patient.

In a majority of patients VT originates from a 1 to 2 mm lesion that is located close to the inner surface of the heart chamber. A treatment of VT in use since 1981 comprises a method whereby electrical pathways of the heart are mapped to locate the lesion, i.e., the "active site," and then the active site is physically ablated. In most instances the mapping and ablation are performed while the patient's chest and heart are open. Also, the mapping procedure has been carried out by sequentially moving a hand-held electrical recording probe or catheter over the heart and recording the times of arrival of electrical pulses to specific locations. These processes are long and tedious.

Attempts to destroy, i.e., ablate, the critical lesion are now quite successful, but are currently limited to a small number of patients who can survive a prolonged procedure during which they have to remain in VT for almost intolerable periods of time. The time-consuming part of the treatment is the localization, i.e., identifying the site, of the target lesion to be ablated. Another limitation preventing the widespread use of catheter ablation for VT is poor resolution of target localization, which in turn compels the physician to ablate a large area of the patient's heart. The reduction in heart function following such ablation becomes detrimental to most patients with pre-existing cardiac damage. However, once the target is correctly identified, ablation is successful in almost all patients.

An improved procedure for treatment of VT must include a faster, more efficient and accurate technique for identifying, or "mapping", the electrical activation sequence of the heart to locate the active site.

In electrophysiologic examinations, and in particular in those using invasive techniques, so-called electrical activation mapping is frequently used in combination with an x-ray transillumination. The local electrical activity is sensed at a site within a patient's heart chamber using a steerable catheter, the position of which is assessed by transillumination images in which the heart chamber is not visible. Local electrical activation time, measured as time elapsed from a common reference time event of the cardiac cycle to a fiducial point during the electrical systole, represents the local information needed to construct the activation map data point at a single location. To generate a detailed activation map of the heart, several data points are sampled. The catheter is moved to a different location within the heart chamber and the electrical activation is acquired again, the catheter is repeatedly portrayed in the transillumination images, and its location is determined. Currently catheter location is determined qualitatively or semi-qualitatively by categorizing catheter location to one of several predetermined locations. Furthermore, the transillumination method for locating the catheter does not convey information regarding the heart chamber architecture.

The present technique requires the use of a transillumination means during each of the subsequent catheter employments. This means that if the subsequent catheter locating is achieved by ionizing radiation, the patient and the physician must be subjected to a radiation exposure beyond that which would be required only for producing the basic image of the heart chamber architecture.

A catheter which can be located in a patient using an ultrasound transmitter allocated to the catheter is disclosed in U.S. Pat. No. 4,697,595 and in the technical note "Ultrasonically marked catheter, a method for positive echographic catheter position identification." Breyer et al., Medical and Biological Engineering and Computing. May, 1985, pp. 268–271. Also, U.S. Pat. No. 5,042,486 discloses a catheter which can be located in a patient using non-ionizing fields and superimposing catheter location on a previously obtained radiological image of a blood vessel. There is no discussion in either of these references as to the acquisition of a local information, particularly with electrical activation of the heart, with the locatable catheter tip and of possible superimposition of this local information acquired in this manner with other images, particularly with a heart chamber image.

OBJECTS OF THE INVENTION

It is an object of the present invention to provide an alternative method for the permanent portrayal of the catheter during mapping procedures by a method making use of non-ionizing rays, waves or fields, and thus having the advantage of limiting the radiation exposure for the patient and the physician.

It is also an object of the invention to provide a catheter locating means and method that will offer quantitative, high-resolution locating information that once assimilated with the sensed local information would result a high-resolution, detailed map of the information superimposed on the organ architecture.

It is a further object of the present invention to provide a mapping catheter with a locatable sensor at its tip.

These and other objects of the invention will become more apparent from the discussion below.

BRIEF DESCRIPTION OF THE DRAWINGS

FIG. 8A is a diagram representing the catheter used for mapping arrhythmias;

FIGS. 8B and 8C represent enlarged sections of the distal and proximal portions, respectively, of the catheter of FIG. 8A.

SUMMARY OF THE INVENTION

Figure 1:
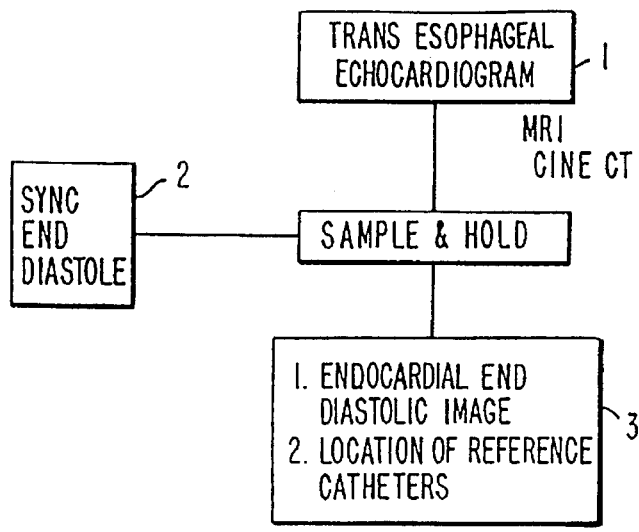
FIG. 1 is a schematic block diagram for acquiring a basic image.

A trackable mapping/ablation catheter, for use with reference catheters in a field such as an electromagnetic or acoustic field, has (i) a transmitting or receiving antenna for the relevant field within its tip, (ii) a sensor at its tip for acquiring local information such as electrical potentials, chemical concentration, temperature, and/or pressure, and (iii) an appropriate port for delivering energy to tissue. Receiving or transmitting antennas for the respective field are attached to the patient in which the catheter is disposed. A receiver or transmitter is connected to these antennas and converts the field waves received into electrical locating or image signals. The sensed local information of each site can be portrayed on a display at the respective locations and combined with an image of the structure acquired in a different manner such as by x-ray, NMR, or ultrasound. The resulting information can be used to map the electrical pathways of the heart to determine the situs of a lesion to be ablated.

DETAILED DESCRIPTION OF THE INVENTION

The above objects of the invention are achieved in a method for real-time portrayal of a catheter in the heart chamber, which makes use of a transmitter for electromagnetic or acoustic waves located at the tip of a catheter, these waves being acquired by a receiving antenna attached to the patient and being converted into electrical image signals. The image of the catheter can then be superimposed on a heart chamber image disclosing wall architecture acquired by same or other means of imaging. In an alternative embodiment, the catheter tip may be a receiving antenna, and the externally applied antennas may be transmitting antennas. The sensor in the catheter tip is designed to acquire the information of interest, and the acquisition of local activity at sites located by the tracking methods is used to map the organ under study.

The aforementioned known electromagnetic or acoustic technology permits a simple portrayal of the catheter, because the catheter differs greatly from its environment (biological tissue) with respect to the interaction of x-rays. The catheter locating technique can be employed with an imaging method and with a corresponding, real-time imaging system which makes use of non-ionizing radiation. The non-x-ray image which portrays the catheter can be combined with an image disclosing heart chamber architecture acquired in an appropriate way. The problem of excess radiation exposure is thus overcome; however, the demands made on the non-ionizing imaging system with respect to its applicability and resolution are rather high.

A further possibility, therefore, is to use the non-ionizing field as part of a locating method, as opposed to an imaging method. Locating methods differ from imaging methods in the following ways: Imaging methods are primarily used to topically correctly portray and resolve a number of subjects or subject points within an image within specific limits. This property is known as the multi-target capability in radar technology and is not present in locating methods. Locating methods operate precisely and unambiguously only in the case wherein a single subject is to be portrayed, i.e., to be located. As an example, the catheter tip is a suitable subject point. The advantage of the locating method is that wave fields can be used wherein the employed wave-length, which is defined by the frequency and phase velocity of the surrounding medium (tissue), can be relatively high, and need not be on the order of magnitude of the locating precision. As is known, range decreases greatly with increasing frequency given non-ionizing waves, such as electromagnetic waves and acoustic waves.

It is thus possible, given the use of a locating method, to make use of relatively long wavelengths, and thus lower frequencies. Moreover, the outlay for signal bandwidth and aperture is much smaller in locating methods than in imaging methods, particularly in view of the spectral (signal) and spatial (aperture) occupation density. It is sufficient to bring the subject point to be located into interaction with only a few extracorporeal aperture support points, for example, three to five transmitters or receivers, given a few discreet frequencies, for example, three to five frequencies. On the basis of this interaction, ranges or range differences with reference to the subject position and the various aperture supporting points, the combination of which makes an unambiguous and exact positional identification (locating) of the subject point possible, are determined by measuring phase relationships or transit time relationships. The subject point, i.e., the catheter tip, must be marked for this purpose in a suitable manner.

As in conventional pathfinder technology, it is necessary that the catheter image and the heart chamber image be combined with each other in a proper three-dimensional correspondence, and it is also necessary that the heart chamber architecture does not displace or deform during the treatment. To correct for displacement of the heart chamber that occurs during the cardiac cycle the catheter location is sampled at a single fiducial point during the cardiac cycle. To correct for displacement of the heart chamber that may occur because of breathing or patient movement, a set of more than two locatable catheters is placed at specific points in the heart chamber during the mapping procedures. The location of these reference catheters supplies the necessary information for proper three-dimensional correspondence of the heart chamber image and the mapping catheter location.

The above principles can be applied for mapping other structures of the body, for example, of the urinary bladder, brain, or gastrointestinal tract. Dependent upon the examination technique, the catheter may be replaced by a needle whose tip is the locatable sensor port.

In a broader perspective the invention encompasses four aspects: the first is intended to process locating information; the second processes sensed electrical information; the third integrates previously processed information; and the fourth processes the integrated information to generate a topographical map of the sensed variable. These aspects are described in more detail below.

Catheters will be introduced percutaneously into the heart chambers. Each catheter will be trackable (using the previously described methodology). Preferably three reference catheters will be left in known landmarks, and a fourth catheter will be used as the mapping/ablation catheter. The locations of the three reference catheters will be used to align the location of the heart chamber relative to its location on the "basic image."

1. Image and Location Processor

Image acquisition: A method and device to acquire images of the heart chambers from available imaging modalities (e.g., fluoroscopy, echo, MRI, etc.). The image is to be acquired with sufficient projections (e.g., bi-plane fluoroscopy, several longitudinal or transverse cross-sections of echocardiography) to be able to perform 3-dimensional reconstructions of the cardiac chambers' morphology.

Images will be acquired at specific times during the ablation procedure: the basic image will be recorded at the beginning of the procedure to allow determination of the cardiac chamber anatomy and of the positions of reference catheters in the heart. This image will be used thereafter as the basic source of information to describe the heart chamber morphology.

The image and location processor identifies (i) the location of chamber boundaries using the methods of edge enhancement and edge detection, (ii) catheter locations relative to the chamber boundaries, and (iii) the dynamics of chamber morphology as a function of the cardiac cycle.

By analyzing the displacement of the catheter tips during the cardiac cycle the image processor will calculate the regional contractile performance of the heart at a given moment during the mapping/ablation procedure. This information will be used to monitor systolic contractile functions before and after the ablation procedure.

The location processor identifies the locations of catheters. The locations of the reference catheters are used to align the current position of the heart chamber with that of the "basic image." Once current location data is aligned with the "basic image," location of the mapping and ablation catheter is identified and reported.

2. Electrophysiologic (EP) Processor

The electrophysiologic signal processor will acquire electrical information from one or more of the following sources:

A. ECG tracings (by scanning the tracing);

B. Body surface ECG recordings, either from a 12-lead system (X,Y,Z orthogonal lead system) or from a modified combination of other points on the patient's torso; and C. Intra-cardiac electrograms, from the ablation/recording catheter, and/or from a series of fixed catheters within the heart chambers.

At each of the mapping/ablation stages, namely, sinus rhythm mapping, pace mapping and VT mapping, the EP processor will determine the local activation time relative to a common fiducial point in time. The local activation time recorded at each stage will furnish part of the information required to construct the activation map (isochronous map).

The electrophysiologic processor will also perform the following signal processing functions:

2.A. Origin Site Determination

Determine the most likely origin site of the patient's arrhythmia based upon the body surface ECG tracings during VT. The most likely VT origin site will be detected by analyzing the axis and bundle morphology of the ECG, and by using the current knowledge of correlation between VT morphology and VT origin site.

2.B. Sinus Rhythm Mapping

2.B.1 Delayed Potential Mapping

Using intracardiac electrograms recorded from the mapping catheter tip during sinus rhythm the EP processor will detect and then measure the time of occurrence of delayed diastolic potentials. Detection of late diastolic activity either by (1) ECG signal crossing a threshold value during diastole; or by (2) modelling the electrical activity at a user-defined normal site and then comparing the modelled signal with the actual signal, and estimating the residual from the normal activity; or by (3) using a band pass filter and searching for specific organized high-frequency activities present during diastole; or by (4) using cross-correlation and error function to identify the temporal position of a user-defined delayed potential template. This analysis will be performed on a beat-by-beat basis, and its results will be available to the next stage of data processing and referred to as the time of delayed potential occurrence.

2.C. Pace Mapping

2.C.1 Correlation Map

In a "pace mapping mode" the ECG processor will acquire ECG data while the patient's heart is paced by an external source at a rate similar to the patient's arrhythmia cycle length. The ECG data will be acquired from the body surface electrograms, and the signal will be stored as a segment of ECG with a length of several cycles. The signal acquired will then be subjected to automatic comparison with the patient's own VT signal (see FIG. 7). The comparison between arrhythmia morphology and paced morphology will be performed in two stages: First, the phase shift between the template VT signal and the paced ECG morphology would be estimated using minimal error or maximal cross-correlation for two signals. Then, using this phase shift estimated from an index ECG channel, the similarity of the VT and the paced ECG morphology will be measured as the average of the cross-correlation or the square error of the two signals of all channels recorded.

This two-stage calculation will be repeated each time using a different ECG channel as the index channel for determining the phase shift.

At the end of this procedure the minimal error or the maximal cross-correlation found will be reported to the operator as a cross-correlation value (ACI) of this pacing site.

2.C.2 Local Latency

The ECG processor will measure the pacing stimulus to ventricular activation. The earliest ventricular activation will be measured from the earliest zero crossing time of the first derivative signal generated from each of the body surface ECG recordings acquired while pacing. This interval will be reported to the operator and will be later used in the process of judging the suitability of the site for ablation.

2.D. VT Mapping

2.D.1 Pre-potential Map

During spontaneous or induced VT the ECG processor will search for a pre-potential present on the mapping/ablation electrode electrogram. The potential will be marked either automatically (by a threshold crossing method, by band pass filtering, or by modelling normal diastolic interval and subtracting the template from the actual diastolic interval recordings) or manually by the user-defined fiducial point on the pre-potential signal. The processor will measure the interval between the time of the pre-potential (PP) signal and that of the earliest ventricular (V) activation as recorded from the body surface tracings, and the interval will be calculated and reported to the user. The ECG processor will report on a beat-by-beat basis the value of the PP-V interval.

2.D.2 Premature Stimuli Local Latency

During VT, when premature extrastimuli will be delivered to the mapping catheter, the ECG processor will detect the time of a single premature signal delivered to the mapping/ablation catheter and the earliest local activation (judged by the presence of non-diastolic activity following a predetermined interval at the mapping/ablation catheter and the presence of a different signal morphology shape and value at the body surface electrograms when compared to their value at one cycle length before that event). The presence of electrical activity on the mapping/ablation electrode and the presence of an altered shape of the body surface morphology will be termed as a captured beat. In the presence of a captured beat the ECG processor will calculate the intervals between the stimulus and the preceding earliest ventricular activation (termed V-S) and the interval between the stimulus and the following earliest activation of the ventricle (termed S-V'). The ECG processor will report these intervals to the user after each extrastimulus delivered. Also, the intervals V-S and S-V' will be graphically plotted as a function describing their dependence. The ECG processor will update the plot after each extrastimulus.

2.D.3 Phase Shifting of VT by Premature Stimuli

The ECG processor will identify the effects of the extrastimulus on the phase shifting of the VT as recorded by body surface electrograms. A user-defined body surfaced channel electrogram of non-paced VT morphology will be used as a template (segment length equal to twice VT cycle length), and the electrogram of the same channel acquired for the same duration following the delivery of an extrastimulus during VT will be used as a test segment. The ECG analyzer will compare the template and the test signal morphologies (using minimal error function or maximal cross correlation) to assure that the VT was not terminated or altered. If VT persists, the ECG analyzer will calculate the phase shift caused by the extrastimulus. Phase shift will be calculated as a part of the VT cycle length needed to be added or subtracted to regularize the VT time series.

2.D.4 VT Termination by Premature Stimuli

The ECG processor will look for a non-capture event following the extrastimulus. In that event the ECG processor will look for alteration in the VT following the extrastimulus delivered. If the VT was terminated (as defined by returning to normal ECG morphology and rate), a note of non-capture termination will be generated by the ECG processor. In case there was no capture but VT morphology did not change, the operator will be notified to change the coupling interval for the coming extrastimuli.

3. Image, Catheter Location and Electrophysiologic Information Integrator

This processor will receive information from the devices described earlier and will attribute the processed electrical information to the specific locations of the heart chamber from which it was recorded. This process will be performed in real time and transferred to the next processor.

Processed electrical information, when combined with its location, generates a map. By use of the previously described variables, the following maps will be generated:

(1) Spatial location of the endocardium;
(2) Sinus rhythm activation map (isochronous map);
(3) Diastolic potential occurrence time isochronal map for sinus rhythm mapping;
(4) Correlation map for pace mapping;
(5) Local latency isochronal map during pace mapping;
(6) Activation time isochronal map during VT; and
(7) Pre-potential isochronal map during VT mapping.

Also, the sites where VT was terminated by a non-captured premature stimulus will be presented.

At each stage (sinus rhythm mapping, pace mapping and VT mapping) after each data point is acquired, all available information is reassessed for two purposes: first, to suggest to the operator the next site for data acquisition, and second, to test the available information to propose a site for ablation.

Figure 2:
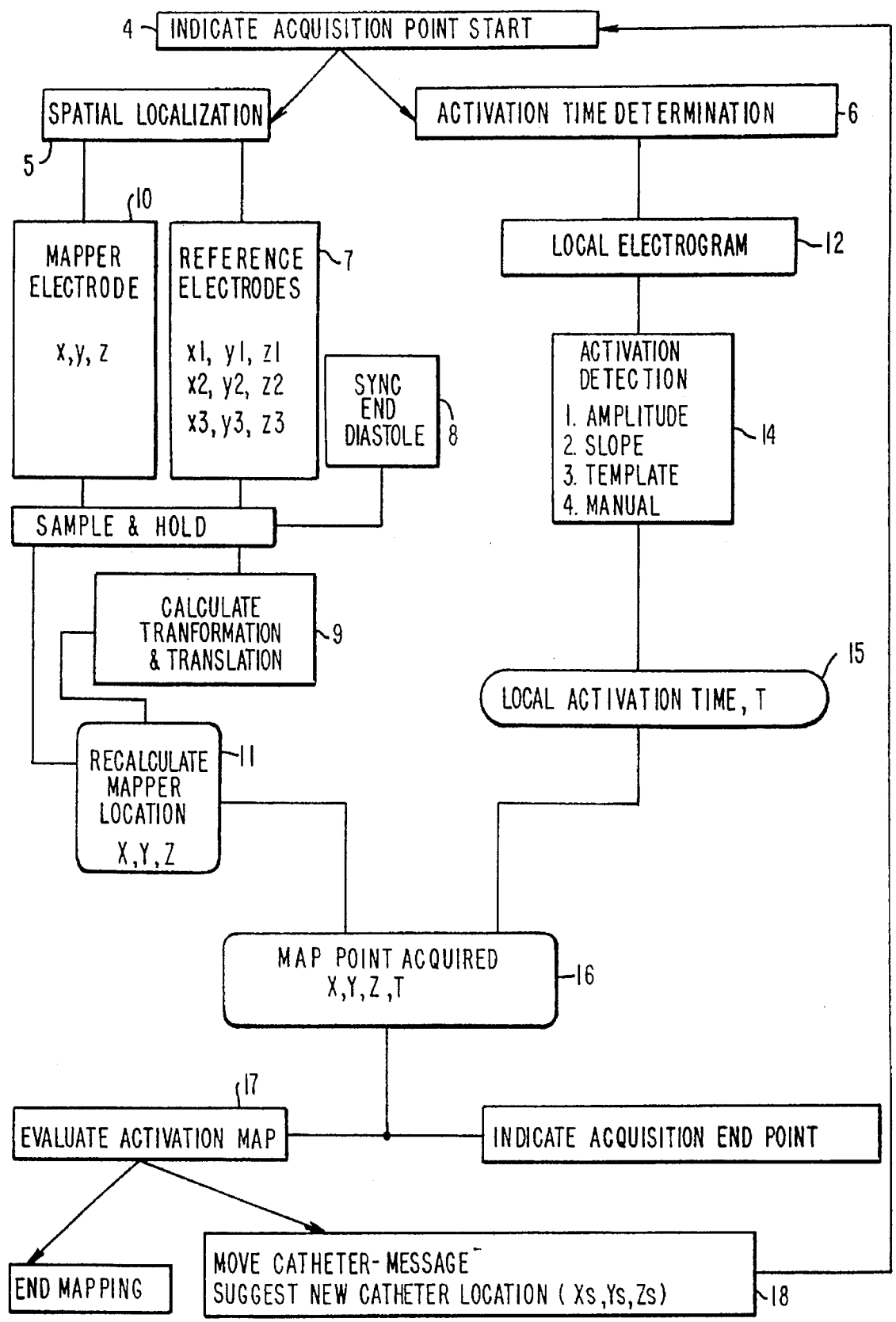
FIG. 2 is a schematic block diagram representing a computerized endocardial mapping algorithm.
Figure 3:
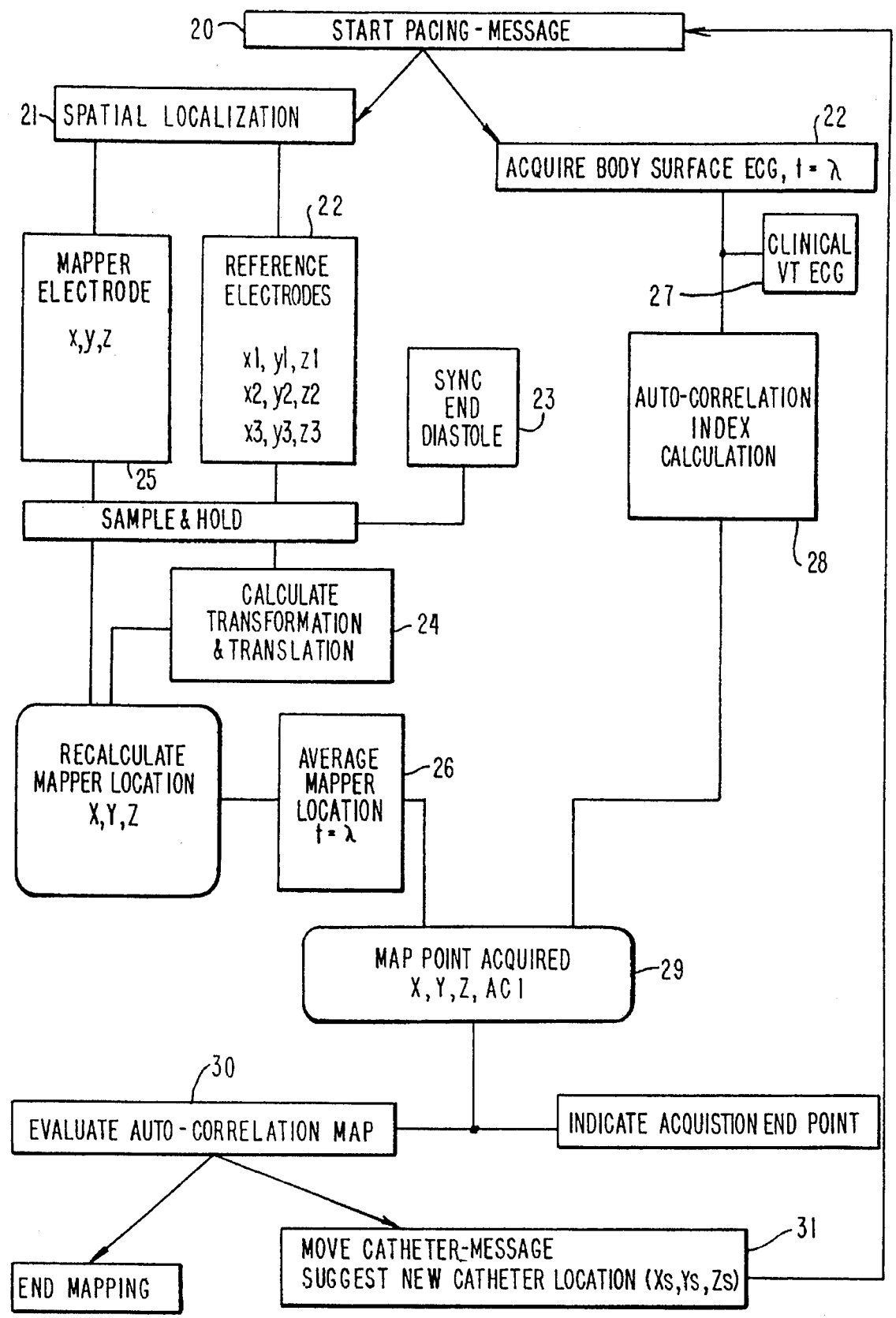
FIG. 3 is a schematic block diagram representing a computerized pace mapping algorithm.

Two algorithms are running simultaneously to perform this procedure:

(1) Mapping guidance algorithm (see Evaluate Activation Map (17) in FIG. 2 and Evaluate Auto-Correlation Map (3a) in FIG. 3). This algorithm uses as an input the available mapped information of a certain variable (e.g., local activation time during sinus rhythm). The algorithm calculates the spatial derivative of the mapped variable (i.e., activation time in this example) and calculates the next best location for adding another data point when the objective function is regularizing the spatial gradients of the mapped variable. For example, this algorithm will suggest that more data points be acquired in areas in which the mapped variable is changing significantly over a short distance.

The location suggested by the algorithm will be presented to the operator as a symbol on the display. The same display already shows the basic image of the heart chamber and the current location of the mapping/ablation catheter. Therefore, the operator will move the mapping/ablation catheter to reach the suggested location for further data acquisition.

This algorithm will become most beneficial during VT mapping, where the available time for data acquisition is limited by the adverse hemodynamic effects of the arrhythmia. Therefore, such an algorithm which examines the available data points of a map in real-time and immediately suggests the next site for acquisition is greatly needed.

(2) Prognosing likelihood of successful ablation algorithm. This algorithm is a user-defined set of hierarchical rules for evaluating the acquired information. The operator is expected to grade the importance of the specific information acquired in the mapping/ablation procedure, as to its likelihood to identify the correct site for ablation. An example of such an algorithm is described in the following section.

Grading of mapping results suggesting the likelihood of successful ablation at that site (A=highly likely successful and D=least likely successful):

(a) The identification of a typical re-entrant pathway on VT mapping with an identifiable common slow pathway—Grade A;
(b) The identification of a site with over 90% correlation index in the pace map—Grade B;
(c) The identification of a site where VT was terminated with a non-capture premature stimulus—Grade C; and
(d) The identification of pre-potential maps recorded during VT, which are similar to diastolic potential maps recorded during sinus rhythm—Grade D.

4. Integrated (Image and Electrical) Processor and Display

The output device will use a computer screen or a holographic imaging unit that will be updated on a beat-by-beat base. The output will include the following information: superimposed on the basic image the position of the catheter will be represented as a symbol on the ventricular wall. The maps will be plotted and overlaid on the same image.

The output device at the mode of guided map acquisition would mark on the ventricular wall image the next best place to position the catheter to acquire ECG information based on the results of the previous analysis.

5. Locatable Catheter Mapping and Ablation Catheters

The catheters used for mapping are critical to the invention. The catheters have a locatable, sensing and/or ablation tip. For locating using electromagnetic fields, locating of the catheter tip is achieved by an antenna disposed at the catheter tip, with an antenna feed guided in or along the catheter. An electrical antenna (dipole) or a magnetic antenna (loop) can be used. The antenna can be operated as a transmission antenna or as a reception antenna, with the extracorporeal antennas located at the skin surface correspondingly functioning as reception antennas or transmission antennas. Given multi-path propagation between the catheter tip and the external antennas, the path between the relevant antennas can be calculated by a suitable multi-frequency or broadband technique. It is also possible to employ the locating method using acoustic waves. The problem of the contrast of the biological tissue is significantly less critical when acoustic waves are used than in the electromagnetic embodiment. The problem of multi-path propagation in the case of acoustic waves, however, will be greater for this embodiment because of the lower attenuation offered by the biological tissue. Both problems, however, can be solved as described above in connection with the electromagnetic embodiment.

A ceramic or polymeric piezoelectric element can be used as the antenna at the catheter tip. Due to the high transmission signal amplitudes, operation of the catheter antenna as a reception antenna is preferred for the case of acoustic locating. Because the transmission paths are reciprocal relative to each other, the locating results are equivalent given reversal of the transmission direction.

The sensor at the catheter tip is constructed with respect to the property to be sensed and the interaction with the locating field waves. For example, a metal electrode for conducting local electrical activity may interact with locating techniques using electromagnetic waves. This problem can be solved in the preferred embodiment by using composite material conductors.

The delivery port at the tip of the catheter is designed with respect to the energy characteristic to be delivered. In the present embodiment the delivery port is the sensing electrode and can function either as an electrode for sensing electrical activity or an antenna to deliver radiofrequency energy to perform ablation of tissue in close contact to the delivery port.

The invention can perhaps be better understood by making reference to the drawings. FIG. 1 is a schematic block diagram for illustrating the acquisition of the basic image. Using a transesophageal echocardiograph (1) in the preferred embodiment, a multiplane image of the heart chambers is acquired prior to the mapping study. The image is acquired only during a fiducial point in time during the cardiac cycle. In the preferred embodiment the image is acquired at end-diastole (2). A three-dimensional image of the heart chambers is reconstructed indicating the endocardial morphology and the location of the reference catheters within the heart chamber (3).

FIG. 2 is a schematic block diagram for illustrating the computerized endocardial activation mapping algorithm (used during sinus rhythm mapping and during ventricular tachycardia mapping). A visible or audible indicator indicates the beginning of a data point acquisition (4). Data is acquired for each point in the map from two sources. The catheter is in steady and stable contact with the endocardium. The mapping catheter tip is localized (5). The localization of the catheter tip involves the localization of the three reference catheters (7). All locating signals are synchronized to end-diastole (8). The transformation of the three reference catheters relative to their original location in the basic image is calculated (9), and the transformation values in the X,Y, and Z as well as the three orientation movements are applied to the measured location of the mapping/ablation catheter (10), the correction of which yields the location of the mapping/ablation catheter with respect to the basic image (11). Electrical activation acquired with the mapping/ablation catheter tip is analyzed in the electrophysiologic signal processor (6). The local electrogram (12), after being filtered, is analyzed to detect the local activation (14) (by one or more of the techniques for amplitude, slope, and template fitting, or by manual detection by the user). The interval elapsed from previous end-diastole to the present local activation is the local activation time (T, 15). The association of the location of the sensor with the activation time generates a single data point for the activation map (16). The process of data acquisition can be terminated by the user, or can be evaluated by the "evaluate activation map" algorithm (17) that examines the already acquired activation map for the density of information relative to the spatial gradient of activation times. This algorithm can indicate the next preferable site for activation time detection (18). The catheter should be moved by the user to the new site, and the process of mapping continues.

During VT a data point is determined about every 4 to 6 beats. Thus, approximately 15 to 25, typically about 20, data points can be determined each minute. This factor, in combination with the remainder of the system described herein, permits faster mapping.

FIG. 3 is a schematic block diagram for illustrating the computerized pace mapping algorithm. A visible or audible indicator indicates the beginning of a data point acquisition (20). Data is acquired for each point in the map from two sources. The mapping/ablation catheter is in steady and stable contact with the endocardium, and the mapping/ablation catheter tip is localized (21). The localization of the catheter tip involves the localization of the three reference catheters (22). All locating signals are synchronized to end-diastole (23). The transformation of the three reference catheters relative to their original location in the basic image is calculated (24), and the transformation values in the X,Y, and Z as well as the three orientation movements are applied to the measured location of the mapping catheter (25), the correction of which yields the location of the mapping/ ablation catheter with respect to the basic image (26). Body surface ECG acquired is analyzed in the electrophysiologic signal processor (22) according to the pace mapping algorithm. The association of the location of the pacing electrode with the cross-correlation index (ACI, 28) of that site yields a single data point of the pace map (29). The process of data acquisition can be terminated by the user, or can be evaluated by the "evaluate pace map" algorithm (30) that examines the already acquired activation map for the density of information relative to the spatial gradient of cross-correlation index, as well as the presence of circumscribed maxima points in the map. This algorithm can indicate the next preferable site for pacing (31). The catheter should be moved by the user to the new site, pace the heart from that new site and calculate the associated cross-correlation index.

Figure 4:
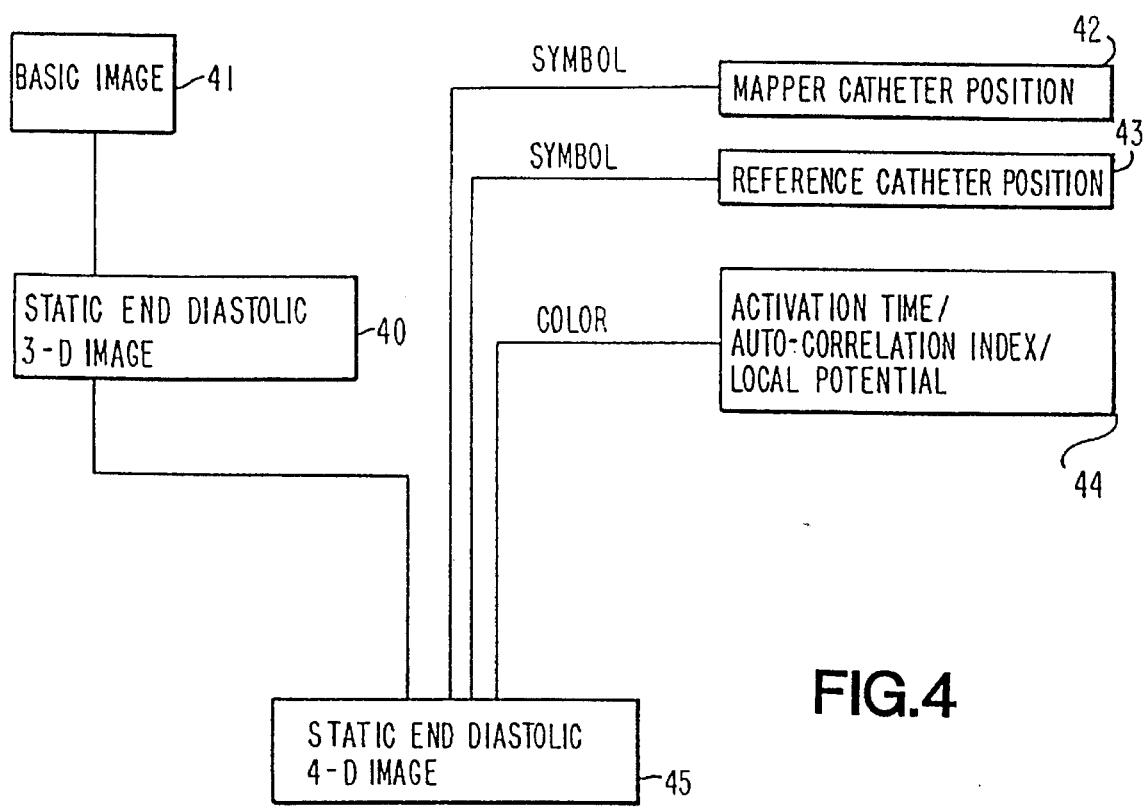
FIG. 4 is a schematic block diagram representing output device configuration of an embodiment of the invention.

FIG. 4 is a schematic block diagram for illustrating the output device configuration (45) of the present embodiment. A quasi-static picture of the heart chambers (40) is presented as 3-D reconstruction of a basic image (41) acquired prior to or during the study. Superimposed on the image (40) will be the location of the mapping/ablation catheter (42), locations of the reference catheters (43), and the current and previous information acquired from the mapping study (44). This information may include, when appropriate, the activation times (presented using a color code at each acquisition site) or cross-correlation index for each point in the pace map. Furthermore, the map can represent in the color coding the duration of the local electrograms, the presence of fragmented activity as well as various other variables calculated by the electrophysiologic processor.

Figure 5:
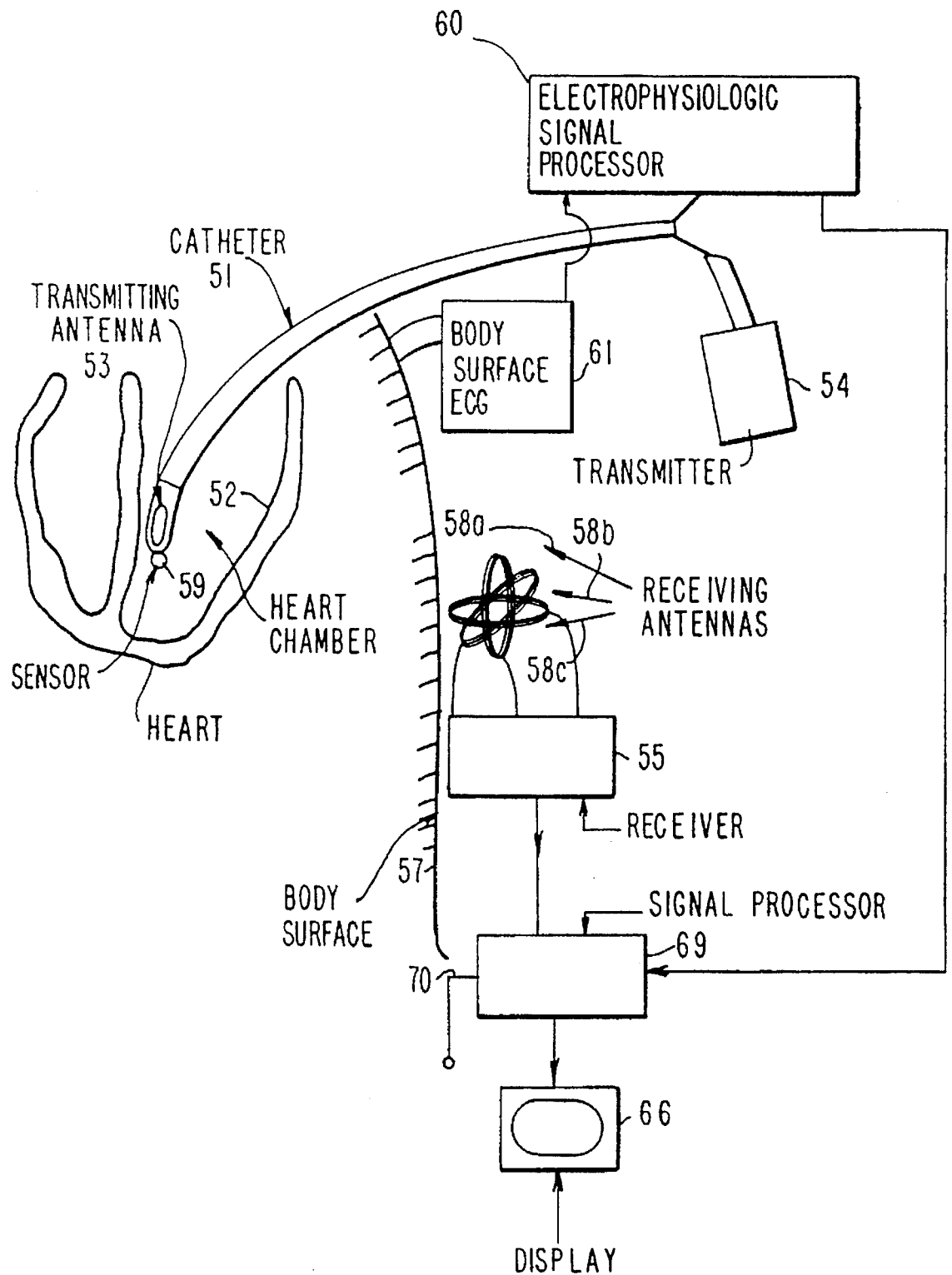
FIG. 5 is a schematic block diagram for illustrating the mapping catheter with the sensor at its tip and a locating method in accordance with the principles of the present invention making use of a transmitting antenna at the catheter tip.

FIG. 5 is a schematic block diagram illustrating the instrument while being used for VT mapping. As shown, a catheter (51) is introduced into the heart chamber (52) in the body of a patient. The catheter (51) has an antenna (53) at its tip, which is supplied with energy by a transmitter (54). The transmitting antenna (53) may be, for example, a dipole. The receiver (55) is provided for locating the position of the tip (53). A receiver (55) receives the electromagnetic waves generated by the antenna (53) by means of a plurality of receiving antennae (58a, 58b, and 58c) placed on the body surface (57) of the patient. A sensor (59) placed on the catheter tip receives local electrical activity of the heart chamber muscle. The signals from the sensor electrode (59) are supplied to an electrophysiologic signal processor (60) which calculates the local activation time delay by subtracting the absolute local activation time from the absolute reference time measured from the body surface electrogram (61) of the present heart cycle. A display (66) permits visual portrayal of the local activation times at the location of the catheter tip as described earlier, for example, by superimposition with an ultrasound image showing the heart chamber architecture. The signals from the receiver (55) and output of electrophysiologic signal processor (60) are supplied to a signal processor (69) which constructs an image of the activation time map.

Information regarding the heart chamber architecture is supplied to the signal processor (69) via a separate input (70). The images are superimposed and are portrayed on the display (66). As noted above, the transmitter and receiver may be an ultrasound transmitter or receiver, instead of electromagnetically operating devices.

Figure 6:
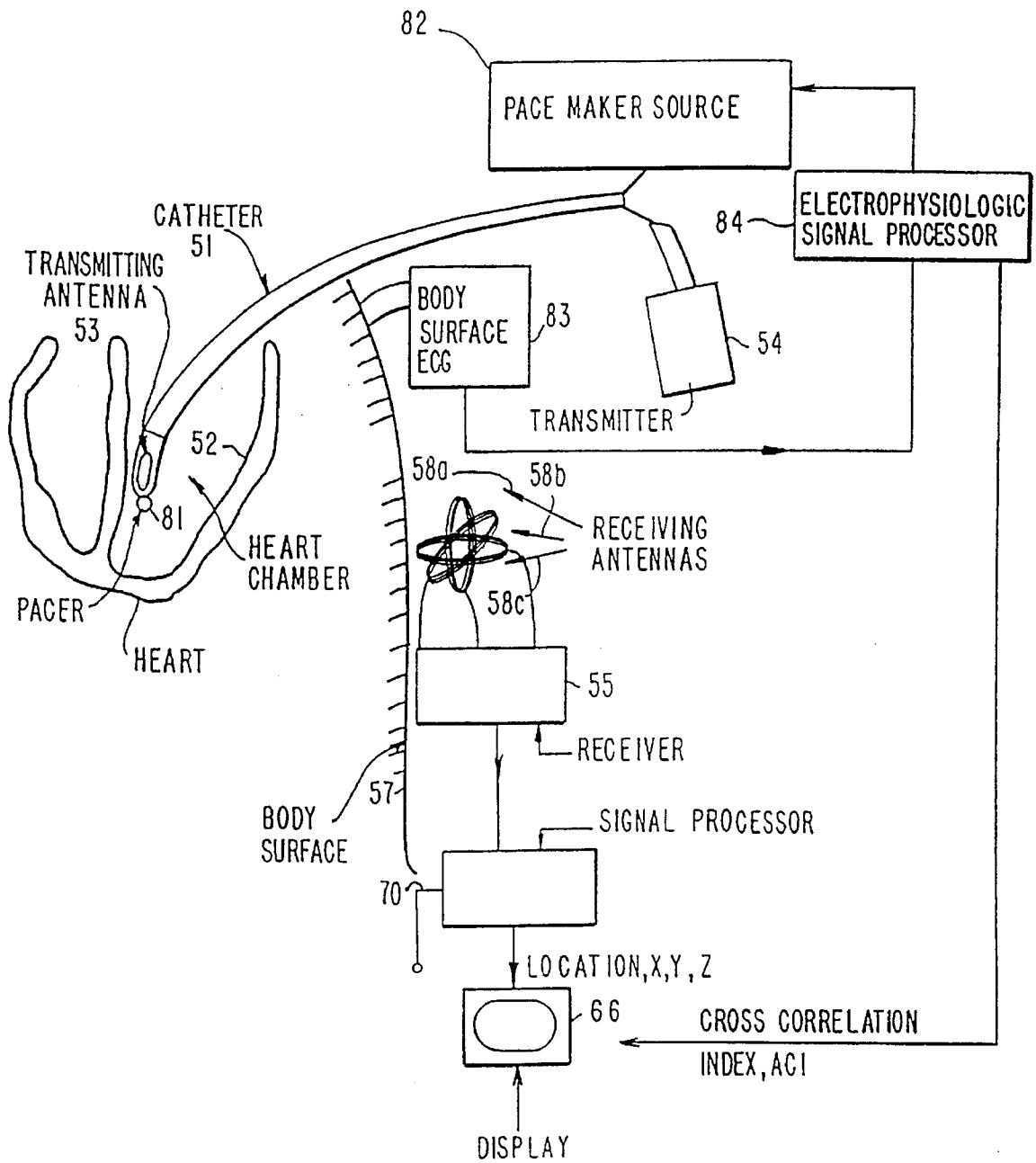
FIG. 6 is a schematic block diagram representing use of the invention for pace mapping.

FIG. 6 is a schematic block diagram illustrating the instrument while being used for pace mapping. The methods for locating catheter tips used in this example are similar to those represented by FIG. 5. Pacing poles (81) are placed on the catheter tip and are connected to a pacemaker (82) source. The pacemaker source activated either by the user or by the electrophysiologic signal processor (84), activates the heart starting at the site of contact of the heart and the pacing poles. Simultaneously acquired ECG (83) is saved and processed in the electrophysiologic signal processor (84). Cross-correlation analysis is carried out in the signal processor (84), and the resulting cross-correlation index (ACI) is transferred to the display unit and associated with the location of the catheter tip to be superimposed on the image of the heart chamber at the appropriate location.

Figure 7:
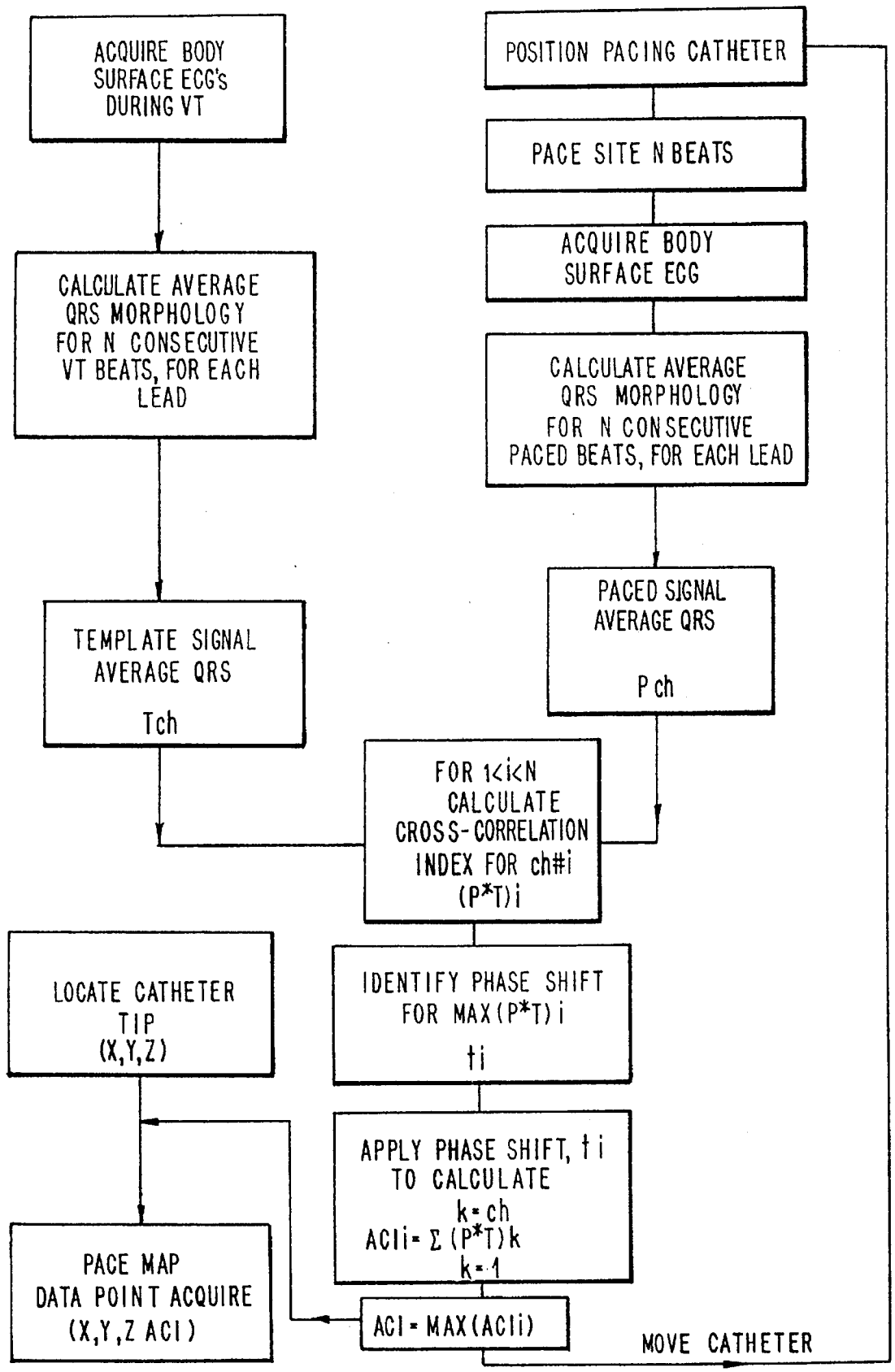
FIG. 7 is a schematic block diagram representing the algorithm used to calculate the cross-correlation index while pace-mapping.

FIG. 7 is a schematic block diagram for illustrating the algorithm used to calculate the cross-correlation index while pace mapping. Body surface ECG data is acquired at two stages. First, during spontaneous or pacing induced VT, and second during pacing the endocardium at different sites. The ECG data acquired during VT are signal averaged, and a template is constructed ($T_{ch}$, for each channel recorded). During endocardial pacing the ECG data is acquired, and the same number of beats (N) is acquired to calculate the signal averaged QRS ($P_{ch}$, for each channel recorded). The algorithm then calculates the phase shift between $P_{ch}$ and $T_{ch}$, which yields for the first channel the maximal cross-correlation. This time shift is used to shift the remaining channels and calculate for them the cross-correlation. All cross-correlations for all channels are summarized and stored. The algorithm then uses the next channel recorded to calculate the time shift that will cause maximal cross-correlation in this channel. Now this time shift is applied for all cross-correlations between $P_{ch}$ and $T_{ch}$, and again all cross-correlations are summarized. This procedure is repeated for all channels, and the maximal cross-correlation achieved is used as the value of the cross-correlation of the $T_{ch}$ and the $P_{ch}$ at this site on the endocardium.

FIG. 8A is a schematic diagram illustrating a catheter (90) used for mapping arrhythmias. The distal catheter tip (91), as shown in FIG. 8B has a conducting material on its outer surface that is the sensing/pacing pole (92) connected to lead (93). In close proximity to pole (92), but separated by insulating material (94), is pole (95), which comprises an annular conducting ring connected to lead (96). The receiver/transmitter antenna (97) of the locating device is placed inside the catheter tip (91), with at least two leads (98) and (99). At least four electrical connections corresponding to leads (93), (96), (98), and (99) exit the catheter: two for the two conducting poles of the sensing/pacing poles and at least two for the locating device antenna. This is shown in FIG. 8C.

Although a multitude of catheters (91) could also be used as reference catheters, a catheter (not shown) having only the receiver/transmitter antenna with leads (98, 99) could function suitably. Also, a mapping/ablation catheter (not shown) could be similar in structure to catheter (90) with an additional lumen or structure or leads to conduct or transmit ablation energy.

Figure 9:
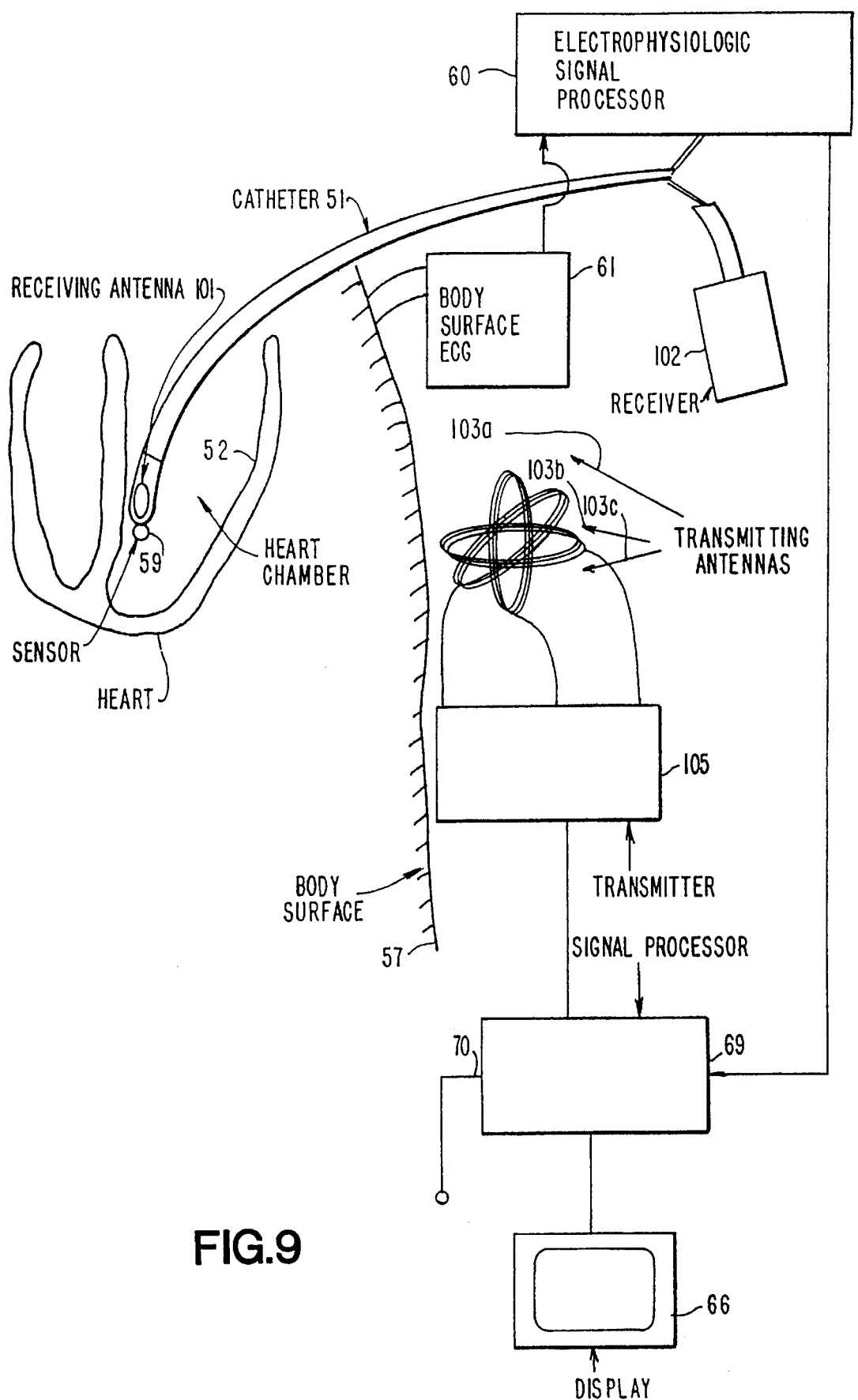
FIGS. 9 and 10 are each a schematic block diagram representing an aspect of the invention.

An alternative embodiment is shown in FIG. 9, wherein the antenna (101) is a receiving antenna. In this embodiment, the antenna (101) is connected to a receiver (102), and the antennas (103a), (103b) and (103c) located at the body surface (57) are transmitting antennas. The transmitter (105) transmits signals to the transmitting antennas (103a), (103b), and (103c). Operation of the method is otherwise identical to that described in connection with FIG. 5. The embodiment of FIG. 9 can be operated as well using acoustic transmission and reception components instead of electromagnetic transmission and reception components.

Figure 10:
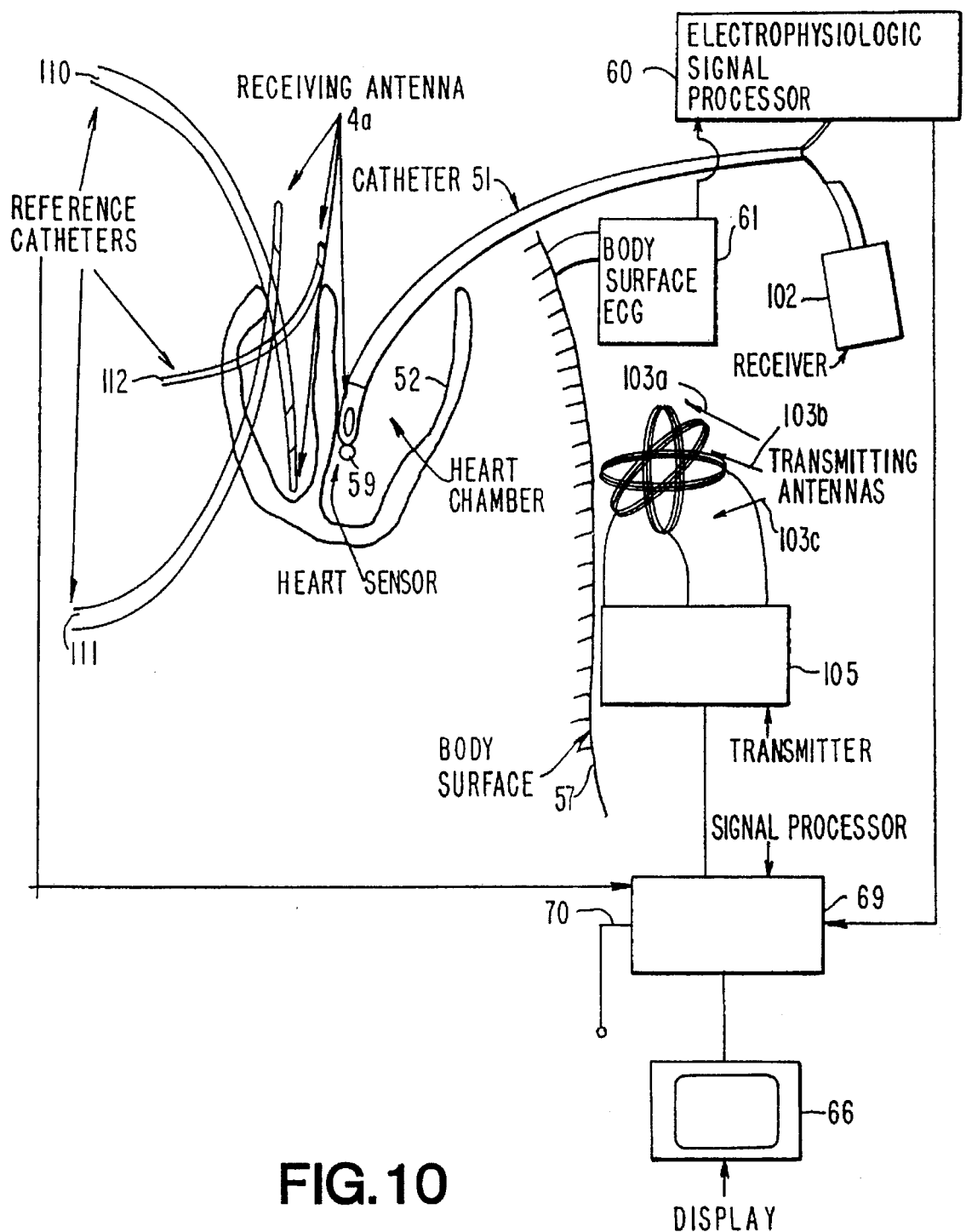

FIG. 10 describes a preferred embodiment of a method for proper three-dimensional correspondence of the catheter tip location and the heart chamber image. Three reference locatable catheters (110), (111), (112), as described in the previous sections of this disclosure are placed in fixed positions in the heart, for example, the right ventricular apex, the right atrial appendage, and the pulmonary artery at the level of the pulmonary valve, respectively. The operation method is similar to that described earlier. The location of these three reference catheters is used by the signal processor (69) for proper three-dimensional correspondence of the heart chamber image and the mapping catheter location.

In one embodiment of the invention the mapping procedure can proceed as follows:

1. Insertion of more than two reference catheters (locatable) to fixed positions in the heart.
2. Acquisition of a "basic image" by an imaging modality such as echocardiogram or MR imaging. Image acquired and 3-D reconstructed at end-diastole.
3. Insertion of mapping/ablation catheter (locatable) and positioning of the catheter in the area suspected by VT morphology to include the "active site."
4. Sinus rhythm mapping to construct sinus rhythm activation maps and diastolic potential isochronal maps.
5. Pace Mapping:
   (a) Construction of ACI map.
   (b) Construction of local latency map.
6. VT Mapping
   (a) Activation mapping: Construction of activation map during VT.
   (b) Pre-potential isochronal map.
   (c) Extrastimuli pacing during VT.
7. Ablation
   (a) Detection of optimal location of ablation from the data acquired with the above mapping.
   (b) Positioning the mapping/ablation catheter on top of the endocardial site;
   (c) Measuring systolic contractile function at that site;
   (d) Delivering ablative energy to the preferred site;
   (e) Repeating step (c)

As can be appreciated, the overall mapping procedure to determine an "active site" is complex and includes several stages, none of which is mandatory. Dependent upon the results obtained in each stage, mapping may continue.

Specific aspects of the procedure can be performed in the following sequence:

Through a percutaneous venous access three reference catheters are introduced into the heart and/or the large vessels. The three reference catheters are positioned so that the respective distal tips are at least 2 cm, preferably 4 to 8 cm, apart. Next, A 3-D image of the chamber of interest is reconstructed using, for example, transesophegeal ultrasonography. Then, the locations of the distal tips of the reference catheters are marked.

Through another vascular access port a mapping/ablation catheter is introduced to the area of interest, and then the location of its distal tip as well as the sensed electrical activity are recorded. The location of the mapping/ablation catheter is measured relative to the location of the reference catheters.

In a modified embodiment of this invention the map previously described can be superimposed on the mapped organ image.

Once the operator identified an active site, the mapping/ablation catheter is positioned so that the active site can be ablated. The ablation is performed by radiofrequency energy. Other known methods could be used instead (e.g., laser, cryotherapy, microwave, etc.).

Although modifications and changes may be suggested by those skilled in the art, it is the intention of the inventor to embody within the patent warranted hereon all changes and modifications as reasonably and properly come within the scope of their contribution to the art.

I claim:

1. A method for intrabody mapping, which comprises the steps of:
   (a) positioning the distal tip of each of one or more catheters at a site adjacent to or within an organ or bodily structure;
   (b) sensing location information at the site using a non-ionizing field;
   (c) sensing local information at the site;
   (d) processing sensed information from steps (b) and (c) to create one or more data points;
   (e) repeating steps (a), (b), (c), and (d) one or more times to create sufficient data points for a map; and
   (f) transmitting said data points from step (e) to a receiving means.

2. A method for intrabody mapping, which comprises the steps of:
   (a) positioning the distal tip of each of one or more catheters at a site adjacent to or within an organ or bodily structure;
   (b) sensing location information at the site;
   (c) sensing local information at the site;
   (d) processing sensed information from steps (b) and (c) to create one or more data points;
   (e) repeating steps (a), (b), (c), and (d) one or more times to create sufficient data points for a map.

3. The method of claim 2 which comprises an additional step (f) wherein said data points or said map is transmitted to receiving means.

4. The method of claim 3 which comprises a further step (g) wherein said data points or said map received by receiving means is projected onto an image receiving means.

5. The method of claim 4 which comprises a yet further step (h) wherein the location of a catheter distal tip is superimposed on said projected map or data points on said image receiving means.

6. A method for intrabody mapping, which comprises the steps of:
   (a) obtaining a perspective image of an organ or bodily structure;
   (b) positioning the distal tip of each of one or more catheters at a site adjacent to or within an organ or bodily structure;
   (c) sensing location information at the site;
   (d) sensing local information at the site;
   (e) processing sensed information from steps (c) and (d) to create one or more data points;
   (f) repeating steps (b), (c), (d), and (e) one or more times to create sufficient data points for a map; and
   (g) superimposing said data points from steps (e) and (f) on the perspective image of the organ or bodily structure.

7. The method of claim 6 which comprises an additional step (h) wherein said data points and said perspective image are transmitted to receiving means.

8. The method of claim 7 which comprises a further step (i) wherein the location of a mapping/ablation catheter distal tip is superimposed on the perspective image of the organ or bodily structure.

9. The method of claim 7 which comprises a further step (i) wherein said data points and said perspective image received by receiving means are projected onto an image receiving means.

10. The method of claim 9 which comprises a yet further step (j) wherein the location of a mapping/ablation catheter distal tip is superimposed on said projected data points and said perspective image on said image receiving means.

11. A method for intrabody mapping, which comprises the steps of:
   (a) positioning the distal tip of each of one or more reference catheters at a site adjacent to or within an organ or bodily structure;
   (b) positioning the distal tip of each of one or more mapping/ablation catheters at a site adjacent to or within an organ or bodily structure;
   (c) sensing location information at each site;
   (d) sensing local information at a site with each mapping/ablation catheter distal tip;
   (e) processing sensed information from steps (c) and (d) to create one or more data points; and
   (f) repeating steps (b), (c), (d), and (e) one or more times to create sufficient data points for a map.

12. The method of claim 11 which comprises an additional step (g) wherein said data points or said map is transmitted to receiving means.

13. The method of claim 12 which comprises a further step (h) wherein said data points or said map received by receiving means is projected onto an image receiving means.

14. The method of claim 13 which comprises a yet further step (i) wherein the location of a mapping/ablation catheter distal tip is superimposed on said projected data points or map on said image receiving means.

15. A method for intrabody mapping, which comprises the steps of:
   (a) positioning the distal tip of each of one or more reference catheters at a site adjacent to or within an organ or bodily structure;
   (b) positioning the distal tip of each of one or more mapping/ablation catheters at a site adjacent to or within an organ or bodily structure;
   (c) sensing location information at each site;
   (d) determining relative location of each mapping/ablation distal tip relative to reference catheter distal tips;
   (e) sensing local information at a site with each mapping/ablation catheter distal tip;
   (f) processing sensed information from steps (d) and (e) to create one or more data points; and
   (g) repeating steps (b), (c), (d), (e), and (f) one or more times to create sufficient data points for a map.

16. The method of claim 15 which comprises an additional step (h) wherein said data points or said map is transmitted to receiving means.

17. The method of claim 16 which comprises a further step (i) wherein said data points or said map received by receiving means is projected onto an image receiving means.

18. The method of claim 17 which comprises a yet further step (j) wherein the location of a mapping/ablation catheter distal tip is superimposed on said projected data points or map on said image receiving means.

19. A method for intrabody mapping, which comprises the steps of:
   (a) obtaining a perspective image of the organ or bodily structure;
   (b) positioning the distal tip of each of one or more reference catheters at a site adjacent to or within an organ or bodily structure;
   (c) positioning the distal tip of each of one or more mapping/ablation catheters at a site adjacent to or within an organ or bodily structure;
   (d) sensing location information at each site;
   (e) sensing local information at a site with each mapping/ablating catheter distal tip;
   (f) processing sensed information from steps (d) and (e) to create one or more data points;
   (g) repeating steps (c), (d), (e), and (f) one or more times to create sufficient data points for a map; and
   (h) superimposing said data points or said map from steps (f) and (g) on the perspective image of the organ or bodily structure.

20. The method of claim 19 which comprises an additional step (i) wherein said data points or map and said perspective image are transmitted to receiving means.

21. The method of claim 20 which comprises a further step (j) wherein said location of a mapping/ablation catheter distal tip is superimposed on said data points or map and said perspective image of the organ or bodily structure.

22. The method of claim 20 which comprises a further step (j) wherein said data points or map and said perspective image received by receiving means are projected onto an image receiving means.

23. The method of claim 22 which comprises a yet further step (k) wherein the location of a mapping/ablation catheter distal tip is superimposed on said projected data points or map and said perspective image on said image receiving means.

24. A method for intrabody mapping, which comprises the steps of:
   (a) obtaining a perspective image of the organ or bodily structure;
   (b) positioning the distal tip of each of one or more reference catheters at a site adjacent to or within an organ or bodily structure;
   (c) positioning the distal tip of each of one or more mapping/ablation catheters at a site adjacent to or within an organ or bodily structure;
   (d) sensing location information at each site;
   (e) determining relative location of each mapping/ablation catheter distal tip relative to reference catheter distal tips;
   (f) sensing local information with each mapping/ablation catheter distal tip;
   (g) processing sensed information from steps (e) and (f) to create one or more data points;
   (h) repeating steps (c), (d), (e), (f) and (g) one or more times to create sufficient data points for a map; and
   (i) superimposing said data points or said map from steps (g) and (h) on the perspective image of the organ or bodily structure.

25. The method of claim 24 which comprises an additional step (j) wherein said data points or map and said perspective image are transmitted to receiving means.

26. The method of claim 25 which comprises a further step (k) wherein the location of a mapping/ablation catheter distal tip is superimposed on the perspective image of the organ or bodily structure.

27. The method of claim 25 which comprises a further step (k) wherein said data points or map and said perspective image received by receiving means are projected onto an image receiving means.

28. The method of claim 27 which comprises a yet further step (l) wherein the location of a mapping/ablation catheter distal tip is superimposed on said projected data points or map and said perspective image on said image receiving means.

29. The method of claim 2, 6, 11, 15, 19, or 24, wherein sensing location information is achieved using a non-ionizing field.

30. An apparatus for intrabody mapping, which comprises:
   (a) means for positioning the distal tip of each of one or more catheters at a site adjacent to or within an organ or bodily structure;
   (b) means for sensing location information at the site using a non-ionizing field;
   (c) means for sensing local information at the site;
   (d) means for processing sensed information from means (b) and (c) to create one or more data points;
   (e) means for repeating the functions of means (a), (b), (c), and (d) one or more times to create sufficient data points for a map; and
   (f) means for transmitting said data points from means (e) to a receiving means.

31. An apparatus for intrabody mapping, which comprises:
   (a) means for positioning the distal tip of each of one or more catheters at a site adjacent to or within an organ or bodily structure;
   (b) means for sensing location information at the site;
   (c) means for sensing local information at the site;
   (d) means for processing sensed information from means (b) and (c) to create one or more data points; and
   (e) means for repeating the functions of means (a), (b), (c), and (d) one or more times to create sufficient data points for a map.

32. The apparatus of claim 31 which additionally comprises means for transmitting said data points or said map to receiving means.

33. The apparatus of claim 32 which further comprises means for projecting said data points or said map received by receiving means onto an image receiving means.

34. The apparatus of claim 33 which yet further comprises means for superimposing the location of a catheter distal tip on said projected map or data points on said image receiving means.

35. An apparatus for intrabody mapping, which comprises:
   (a) means for obtaining a perspective image of an organ or bodily structure;
   (b) means for positioning the distal tip of each of one or more catheters at a site adjacent to or within an organ or bodily structure;
   (c) means for sensing location information at the site;
   (d) means for sensing local information at the site;
   (e) means for processing sensed information from means (c) and (d) to create one or more data points;
   (f) means for repeating the functions of means (b), (c), (d), and (e) one or more times to create sufficient data points for a map; and
   (g) means for superimposing said data points from means (e) and (f) on the perspective image of the organ or bodily structure.

36. The apparatus of claim 35 which additionally comprises means for transmitting said data points and said perspective image to receiving means.

37. The apparatus of claim 36 which further comprises means for superimposing the location of a mapping/ablation catheter distal tip on the perspective image of the organ or bodily structure.

38. The apparatus of claim 36 which further comprises means for projecting said data points and said perspective image received by receiving means onto an image receiving means.

39. The apparatus of claim 38 which yet further comprises means for superimposing the location of a mapping/ablation catheter distal tip on said projected data points and said perspective image on said image receiving means.

40. An apparatus for intrabody mapping, which comprises:
   (a) means for positioning the distal tip of each of one or more reference catheters at a site adjacent to or within an organ or bodily structure;
   (b) means for positioning the distal tip of each of one or more mapping/ablation catheters at a site adjacent to or within an organ or bodily structure;
   (c) means for sensing location information at each site;
   (d) means for sensing local information at a site with each mapping/ablation catheter distal tip;
   (e) means for processing sensed information from means (c) and (d) to create one or more data points; and
   (f) means for repeating the functions of means (b), (c), (d), and (e) one or more times to create sufficient data points for a map.

41. The apparatus of claim 40 which additionally comprises means for transmitting said data points or said map to receiving means.

42. The apparatus of claim 41 which further comprises means for projecting said data points or said map received by receiving means onto an image receiving means.

43. The apparatus of claim 42 which yet further comprises means for superimposing the location of a mapping/ablation catheter distal tip on said projected data points or map on said image receiving means.

44. An apparatus for intrabody mapping, which comprises:
   (a) means for positioning the distal tip of each of one or more reference catheters at a site adjacent to or within an organ or bodily structure;
   (b) means for positioning the distal tip of each of one or more mapping/ablation catheters at a site adjacent to or within an organ or bodily structure;
   (c) means for sensing location information at each site;
   (d) means for determining relative location of each mapping/ablation distal tip relative to reference catheter distal tips;
   (e) means for sensing local information at a site with each mapping/ablation catheter distal tip;
   (f) means for processing sensed information from means (d) and (e) to create one or more data points; and
   (g) means for repeating the functions of means (b), (c), (d), (e), and (f) one or more times to create sufficient data points for a map.

45. The apparatus of claim 44 which additionally comprises means for transmitting said data points or said map to receiving means.

46. The apparatus of claim 45 which further comprises means for projecting said data points or said map received by receiving means onto an image receiving means.

47. The apparatus of claim 46 which yet further comprises means for superimposing the location of a mapping/ablation catheter distal tip on said projected data points or map on said image receiving means.

48. An apparatus for intrabody mapping, which comprises:
   (a) means for obtaining a perspective image of the organ or bodily structure;
   (b) means for positioning the distal tip of each of one or more reference catheters at a site adjacent to or within an organ or bodily structure;
   (c) means for positioning the distal tip of each of one or more mapping/ablation catheters at a site adjacent to or within an organ or bodily structure;
   (d) means for sensing location information at each site;
   (e) means for sensing local information at a site with each mapping/ablation catheter distal tip;
   (f) means for processing sensed information from means (d) and (e) to create one or more data points;
   (g) means for repeating the functions of means (c), (d), (e), and (f) one or more times to create sufficient data points for a map; and
   (h) means for superimposing said data points or said map from means (f) and (g) on the perspective image of the organ or bodily structure.

49. The apparatus of claim 48 which additionally comprises means for transmitting said data points or map and said perspective image to receiving means.

50. The apparatus of claim 49 which further comprises means for superimposing said location of a mapping/ablation catheter distal tip on said data points or map and said perspective image of the organ or bodily structure.

51. The apparatus of claim 49 which further comprises means for projecting said data points or map and said perspective image received by receiving means onto an image receiving means.

52. The apparatus of claim 51 which yet further comprises means for superimposing the location of a mapping/ablation catheter distal tip on said projected data points or map and said perspective image on said image receiving means.

53. An apparatus for intrabody mapping, which comprises:
   (a) means for obtaining a perspective image of the organ or bodily structure;
   (b) means for positioning the distal tip of each of one or more reference catheters at a site adjacent to or within an organ or bodily structure;
   (c) means for positioning the distal tip of each of one or more mapping/ablation catheters at a site adjacent to or within an organ or bodily structure;
   (d) means for sensing location information at each site;
   (e) means for determining relative location of each mapping/ablation catheter distal tip relative to reference catheter distal tips;
   (f) means for sensing local information with each mapping/ablation catheter distal tip;
   (g) means for processing sensed information from means (e) and (f) to create one or more data points;
   (h) means for repeating the functions of means (c), (d), (e), (f) and (g) one or more times to create sufficient data points for a map; and
   (i) means for superimposing said data points or said map from means (g) and (h) on the perspective image of the organ or bodily structure.

54. The apparatus of claim 53 which additionally comprises means for transmitting said data points or map and said perspective image to receiving means.

55. The apparatus of claim 54 which further comprises means for superimposing the location of a mapping/ablation catheter distal tip on the perspective image of the organ or bodily structure.

56. The method of claim 54 which further comprises means for projecting said data points or map and said perspective image received by receiving means onto an image receiving means.

57. The apparatus of claim 56 which yet further comprises means for superimposing the location of a mapping/ablation catheter distal tip on said projected data points or map and said perspective image on said image receiving means.

58. The apparatus of claims 31, 35, 40, 44, 48, or 53, wherein location information is sensed using a non-ionizing field.

* * * * *